(12) United States Patent
Schaeffer

(10) Patent No.: US 8,123,681 B2
(45) Date of Patent: Feb. 28, 2012

(54) MEDICAL APPLIANCE STABILIZATION DEVICE AND METHOD FOR USING SAME

(75) Inventor: Rodney D. Schaeffer, Lead, SD (US)

(73) Assignee: Rodney D. Schaeffer, Spearfish, SD (US)

( * ) Notice: Subject to any disclaimer, the term of this patent is extended or adjusted under 35 U.S.C. 154(b) by 0 days.

(21) Appl. No.: 12/284,818

(22) Filed: Sep. 25, 2008

(65) Prior Publication Data

US 2009/0105656 A1 Apr. 23, 2009

Related U.S. Application Data

(60) Provisional application No. 60/999,678, filed on Oct. 19, 2007.

(51) Int. Cl.
*A61M 5/32* (2006.01)
(52) U.S. Cl. ........ 600/179; 604/174; 604/178; 604/189; 606/108
(58) Field of Classification Search ................ 604/174, 604/178, 179, 189; 606/108; 128/95.1, 112.1, 128/115.1, 846, 847, 852
See application file for complete search history.

(56) References Cited

U.S. PATENT DOCUMENTS

| | | |
|---|---|---|
| 3,194,235 A | 7/1965 | Cooke |
| 3,196,870 A | 7/1965 | Sprecher et al. |
| 3,376,865 A | 4/1968 | Gamper |
| 3,423,095 A | 1/1969 | Cox |
| 3,633,567 A | 1/1972 | Sarnoff |
| 3,640,273 A | 2/1972 | Ray |
| 3,719,187 A | 3/1973 | Ulansey |
| 3,722,508 A | 3/1973 | Roberts |
| 3,745,998 A | 7/1973 | Rose |
| 3,814,080 A | 6/1974 | Norman |
| 3,815,588 A | 6/1974 | Klausner |
| 3,827,107 A | 8/1974 | Moore |
| 4,048,991 A | 9/1977 | Marx |
| 4,149,540 A | 4/1979 | Hasslinger |
| 4,151,842 A | 5/1979 | Miller |
| 4,198,989 A | 4/1980 | Hawke et al. |
| 4,224,937 A | 9/1980 | Gordon |

(Continued)

FOREIGN PATENT DOCUMENTS

FR 1003251 12/1951

OTHER PUBLICATIONS

International Search Report and Written Opinion of PCT/US2008/011846 dated Dec. 3, 2008.

(Continued)

*Primary Examiner* — Bhisma Mehta
*Assistant Examiner* — Larry R Wilson
(74) *Attorney, Agent, or Firm* — McQuaide Blasko, Inc.

(57) ABSTRACT

Systems and methods for achieving stabilization of medical devices, both invasive and non-invasive, are provided for human and veterinary subjects. The stabilization device comprises a platform for being positioned on a body part, a hooking apparatus positioned within an inner surface of the platform, and at least one securing strap attached to the platform. The durable stabilization device can be rapidly deployed under sterile and field emergency conditions to provide a high level of stability to medical appliances, and is easily removable from a body part of a subject without causing discomfort or damage to the integument or other tissues.

16 Claims, 5 Drawing Sheets

U.S. PATENT DOCUMENTS

| | | | |
|---|---|---|---|
| 4,273,130 A | 6/1981 | Simpson | |
| 4,436,088 A | 3/1984 | Finnieston | |
| 4,453,933 A | 6/1984 | Speaker | |
| 4,502,477 A | 3/1985 | Lewis | |
| 4,606,735 A | 8/1986 | Wilder et al. | |
| 4,633,863 A | 1/1987 | Filips et al. | |
| 4,671,787 A | 6/1987 | Widman | |
| 4,675,015 A | 6/1987 | Brown | |
| 4,717,385 A * | 1/1988 | Cameron et al. | 604/174 |
| 4,870,976 A | 10/1989 | Denny | |
| 4,898,587 A | 2/1990 | Mera | |
| 4,919,150 A | 4/1990 | Grant | |
| 4,928,712 A | 5/1990 | Mele | |
| 5,084,026 A | 1/1992 | Shapiro | |
| 5,238,010 A | 8/1993 | Grubenkort et al. | |
| 5,266,401 A | 11/1993 | Tollini | |
| 5,312,365 A * | 5/1994 | Firth et al. | 604/189 |
| 5,339,834 A | 8/1994 | Marcelli | |
| 5,413,120 A | 5/1995 | Grant | |
| 5,577,516 A * | 11/1996 | Schaeffer | 128/877 |
| 5,728,053 A | 3/1998 | Calvert | |
| 5,769,804 A | 6/1998 | Harris et al. | |
| 5,897,519 A | 4/1999 | Shesol et al. | |
| 6,042,568 A | 3/2000 | Gomez | |
| 6,047,699 A * | 4/2000 | Ryatt et al. | 128/207.17 |
| 6,053,170 A | 4/2000 | Padilla, Jr. | |
| 6,257,240 B1 | 7/2001 | Shesol | |
| 6,258,066 B1 | 7/2001 | Urich | |
| 6,267,115 B1 * | 7/2001 | Marshel | 128/877 |
| 6,500,154 B1 | 12/2002 | Hakky et al. | |
| 6,526,981 B1 | 3/2003 | Rozier et al. | |
| D541,934 S | 5/2007 | Gomez | |
| 2003/0055382 A1 * | 3/2003 | Schaeffer | 604/179 |
| 2007/0088280 A1 * | 4/2007 | Gomez | 604/174 |

OTHER PUBLICATIONS

International Preliminary Report on Patentability for PCT/US2008/011846, Apr. 29, 2010.

* cited by examiner

MEDICAL APPLIANCE STABILIZATION DEVICE AND METHOD FOR USING SAME

RELATED APPLICATIONS

This application claims priority to U.S. Provisional Application No. 60/999,678, filed Oct. 19, 2007.

INTRODUCTION

The present teachings are directed to systems and methods for achieving stabilization of medical devices, both invasive and non-invasive, for human and veterinary subjects. The present teachings are further directed to a stabilization device that can be rapidly deployed under sterile and field emergency conditions to attach and stabilize myriad invasive and non-invasive medical appliances, including intravenous catheters and tubing.

Medical devices that require application to a body part of a subject are ubiquitous. Examples of invasive medical devices include intravenous (IV) catheters and tubing, urinary catheters, and wound drainage systems. Non-invasive devices include oxygen and cardiac monitoring systems. In each of the foregoing instances, the medical devices are positioned on and secured to the body of a subject by means of adhesive tape, bandages, cloth, or similar flexible mechanism (collectively referred to as "adhesive").

The current adhesives have several disadvantages. One disadvantage of such practices is that clean and dry surface conditions are required for successful application of an adhesive to a subject's body. The integrity of an adhesive seal is comprised in the presence of lesions, wounds, burns or otherwise non-intact skin. Similarly, foreign contaminants such as blood, hair, fur, feathers, diaphoresis, sand, gravel, grass, or other surface objects create suboptimal adhesive surfaces. The foregoing contaminants, however, are routinely found at medical device application sites or insertion points, especially in field emergency conditions.

Another disadvantage of the current adhesives is their difficulty of application. During IV catheter insertion, for example, a medical worker is required to hold and insert a catheter and tubing with one hand, while preparing and applying an adhesive to the skin of his or her subject with the other hand. These tasks are difficult and time consuming to perform with one hand, particularly in emergency situations. Frequently, the medical worker must either release the subject's body part or obtain the assistance of other personnel to secure the catheter and IV tubing to the insertion site. During emergencies, a medical worker may not be able to release an individual's body part or obtain the assistance of other personnel.

A further disadvantage of the current adhesives involves their lack of stabilization strength. Most adhesives are not designed to strongly adhere to the skin of a human or veterinary subject, and frequently separate from the skin. As a consequence, medical devices are often dislodged from their placement or insertion sites in response to minimal movements such as the daily routine of a subject, the jostling of a subject during transport, or scheduled care giving. Moreover, foreign contaminants may come into contact with the skin or underlying tissue of a subject.

In instances where the adhesive used to secure a medical appliance to a subject does not fail, a principal drawback is that the adhesive strength tends to be excessive. Intentional removal of the adhesive from the subject frequently results in damage to or disintegration of the integument and underlying tissue at the medical device placement site or insertion point. Occasionally, adhesive removal induces lacerations in the dermis of a subject, resulting in lesion or wound formation. This is typically encountered in individuals who are bedridden, and in elderly individuals who have skin that has weakened with age. In compromised patients, skin abrasion and wound occurrence complicate medical management and recovery time and increase overall health care risks and costs.

A yet further disadvantage of current stabilization practices relates to the high incidence of allergic sensitivity to adhesives. Some individuals develop dermatitis, rashes, or other skin irritations when exposed to adhesives. Other individuals develop seeping wounds due to the repeated application and removal of adhesive to the patients' skin. Such complications greatly increase patient discomfort and extend the lengths of hospital admissions.

Accordingly, there is a need for an apparatus that is durable, readily deployable during emergency situations as well as in controlled medical environments, and that is capable of securing a medical appliance to a subject without damage to its integument or other tissue.

SUMMARY

The present teachings disclose medical appliance stabilization devices and methods for using same. The durable stabilization device can be readily deployed in any environment, provides a high level of stability to both invasive and non-invasive medical appliances, and is easily removable from a body part of a subject without causing discomfort or damage to the integument or other tissues. The stabilization device comprises a generally planar platform having a perforate inner surface, an outer surface, and an underside having a non-stick surface that is positioned adjacent a body part when securing a medical appliance in engagement with the body part. One or more securing apparatus are attached to the device for being arranged about the body part and for retaining the platform non-stick surface adjacent the body part.

These and other features of the present teachings are set forth herein.

BRIEF DESCRIPTION OF THE DRAWINGS

The skilled artisan will understand that the drawings described below are for illustration purposes only. The drawings are not intended to limit the scope of the present teachings in any way.

DESCRIPTION OF VARIOUS EMBODIMENTS

Figure 1:
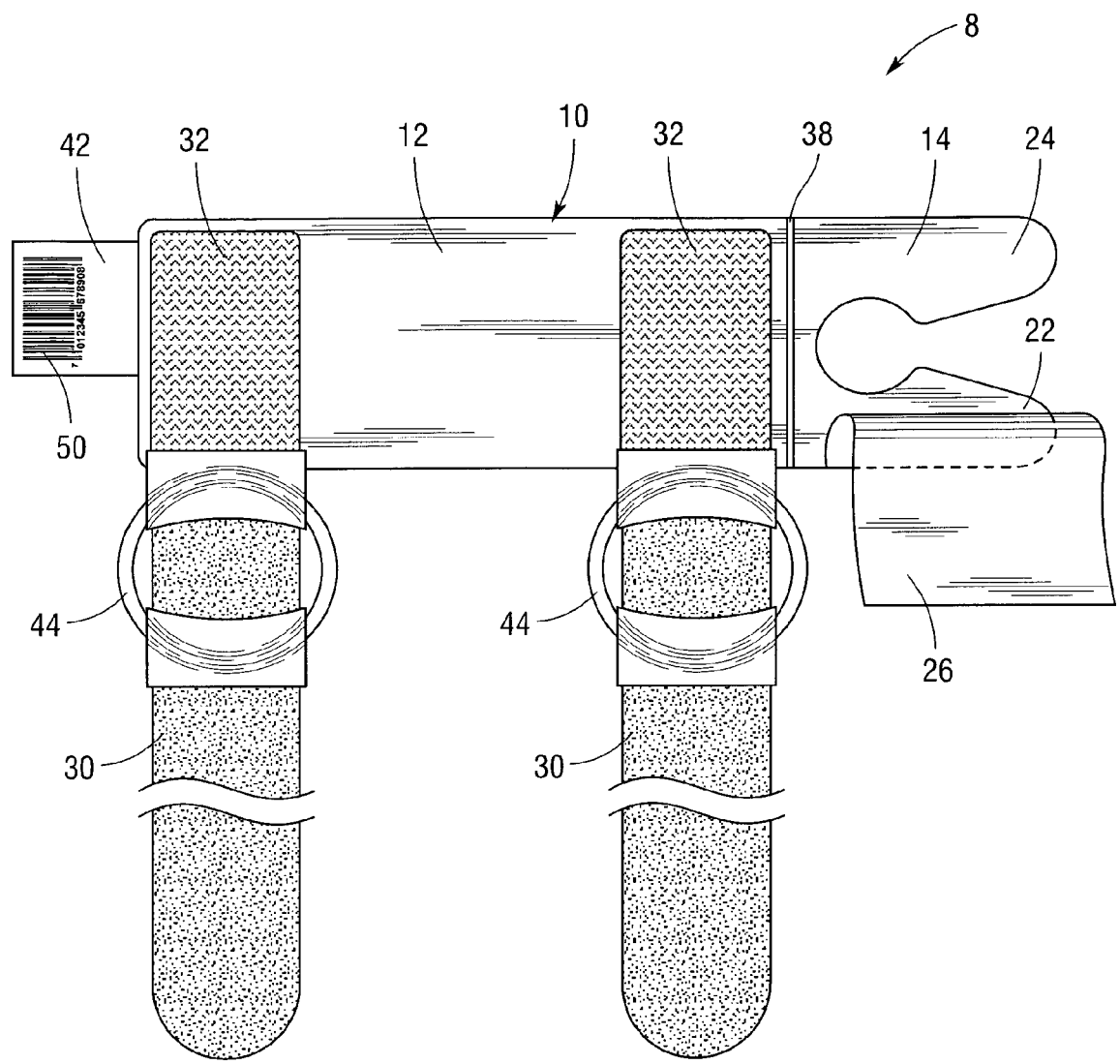
FIG. 1 is a top plan view of a stabilization device shown with a hook member in accordance with the present teachings.

As described above, the present teachings disclose devices and methods for rapidly attaching and stabilizing a plurality of invasive and non-invasive medical appliances.

As referred to in this application, the term "medical appliance" refers to invasive devices such as intravenous catheters and tubing, urinary catheters, catheter leads, pacemaker and defibrillator leads, and wound drainage systems. The term also refers to non-invasive devices such as oxygen and cardiac monitoring systems.

Referring now to the Figures, there is shown a device 8 for stabilizing a medical appliance on a body part of a subject in accordance with the present teachings. The stabilization device 8 includes a base or platform 10 having a perforate inner surface 12 bordered by an outer surface 14 having corresponding edges. The inner 12 and outer 14 surfaces are disposed on an upper plane 20 of the platform 10. In various embodiments, the outer surface 14 edges are blunted or are curled to avoid any undue sharpness or discomfort to a user. In various embodiments, the platform 10 further includes an underside comprising a non-stick surface 16 that is positioned adjacent a body part when securing a medical appliance in engagement with the body part. The platform 10 provides a high level of stability to a medical appliance being applied to a body part of a subject without the application of adhesives to the integument.

As referred to in this application, the "platform" 10 comprises a generally longitudinally extending object to which arms 22, 24 of the stabilization device 8 are attached. While the exact shape of the platform 10 can vary widely, a generally planar or comparable configuration is typical. Other geometries may be employed, however, as may be appropriate for certain medical appliances. The platform 10 can be of any length that is compatible overall with the dimensions and type of medical appliance to be stabilized. Determinations relative to size of the platform 10 can also take into account the type of subject (i.e., human or animal) and the size or age of the subject.

The platform 10 can be fabricated of any durable material of sufficient strength, rigidity, and flexibility for a desired application. Such materials include, but are not limited to, plastic, polycarbonate, polymer, rubber, dense foam, acrylic, polystyrene, synthetic resin, nylon, aluminum, sheet metal, composite, and combinations thereof. In some embodiments, medical-grade or U.S. Food and Drug Administration (FDA)-compliant materials are employed for use of the medical appliance stabilization device 8 in human subjects. In some embodiments, the platform 10 comprises approximately four millimeters thick polycarbonate, and the platform 10 is translucent to permit observation therethrough. Any number of techniques known in the art can be used to fabricate the integral platform 10, including, for example, molding, stamping, thermal forming, and punch forming.

In various embodiments, one or more optional fasteners or bonding agents 26 designed to be in engagement with a medical appliance connected to a body part are secured to the upper plane 20 of the platform 10. The fastener 26 serves to support and hold at least a portion of a medical appliance in place on the platform 10. The fastener 26 can be attached at several locations along the stabilization device 8. In some embodiments, the fastener 26 is attached to an edge or to an arm 22, 24 of the platform 10. In some embodiments, the fastener 26 is attached proximate an interior window 28 of the platform 10. The fastener 26 includes a fixed section that is secured to the platform 10 and a moveable section extending from the fixed section. When in use, the fastener 26 comfortably secures a medical appliance in firm engagement with the platform 10, while one or more securing straps 30 retain the stabilization device 8 in place on a body part of a subject. An operator simply releases and pulls the moveable section of fastener 26 about a selected medical appliance, and a mating or bonding surface of fastener 26 is placed in contact with the appliance and an exposed opposing surface of the platform 10.

At least a portion of the fastener 26 can include a bonding surface thereon for mating with a surface of a medical appliance and an exposed opposing surface (e.g., an arm 22, 24 or an edge) of the platform 10. In some embodiments, the fastener 26 comprises, for example, medical-grade tape, one or two-sided adhesive tape, bandages and the like. Similarly, the fastener 26 can be at least partially covered with a detachable liner 46, which is removed during use to expose a bonding surface. It will be appreciated that the bonding surface of fastener 26 does not come into contact with a body part of the subject due to the intervening platform 10. In some embodiments, a fastener 26 such as cloth can be attached to the platform 10 for securing a medical appliance connected to a body part to the platform 10. In some embodiments, the fastener 26 is generally transversely attached to the platform 10, whereby a moveable section extends from the fixed section generally perpendicular to a longitudinal axis of the platform 10. It will be understood, however, that the fastener 26 may be attached and extend parallel to a longitudinal axis of the platform 10.

As described above, the optional fastener 26 is utilized on the upper plane 20 of and in cooperation with the platform 10 of stabilization device 8 which, in turn, is in contact with the body part of a subject. The intervening platform 10, comprising a non-stick surface on the underside 16 thereof, overlays and protects the body part such that tape, bandages, and similar adhesive materials are unable to achieve contact with the dermis, fur, or other body tissue. Therefore, it will be appreciated that the non-stick underside 16 of the platform 10 remains in direct contact with a body part of the subject while a medical appliance—retained in place by the fastener 26—is in engagement with the platform 10.

As may be recognized, the application and removal of adhesive from a subject's skin or fur frequently induces allergic sensitivities and/or disintegration of dermal tissue at the adhesive point of contact and/or medical device insertion point. The platform 10 of stabilization device 8 prevents a fastener bearing adhesive from coming into contact with the skin or fur of a subject. It will therefore be appreciated that the stabilization device 8 of the present teachings protects the integument and underlying tissue of a subject from irritation, abrasion and wound formation. The avoidance of such complications greatly increases patient comfort and decreases the length of hospital admissions. Moreover, the stabilization device 8 is beneficial for use in patient populations that have compromised skin integrity (e.g., the elderly).

In various embodiments, one or more straps, buckles, or hook-and-loop fasteners 30 (collectively referred to herein as "straps" or "securing apparatus") are affixed to the outer surfaces 14 of the platform 10 for retaining the non-stick underside 16 of stabilization device 8 adjacent the body part of a subject. In some embodiments, the straps 30 are flexible such that the pressure at which the straps engage a user's body part can be adjusted. In use, the straps 30 are engaged, arranged about a body part, and pulled taut to hold the stabilization device 8 in place around a body part, at a position selected by the user or medical personnel. Once in place, the platform 10 is interposed medial to the body part and portions of the securing apparatus 30.

Each securing apparatus 30 includes a fixed portion which is secured to the platform 10 and a moveable portion extending from the fixed portion. A distal section of the moveable portion includes a closure member or hook 34 that mates with a corresponding closure segment 32 secured to an exposed surface of the platform 10. In some embodiments, the moveable portion is rolled and/or detachably secured to the outer surface 14 of the platform 10. The moveable portion of the securing apparatus 30 can be quickly unfurled after being released, placed around a body part, and secured to the closure segment 32 on the platform 10. In some embodiments, the straps 30 are generally transversely attached to the platform 10, whereby a moveable portion extends from the fixed portion generally perpendicular to a longitudinal axis of the platform 10. It will be understood, however, that the securing apparatus 30 may be attached and extend parallel to a longitudinal axis of the platform 10.

In some embodiments of the present teachings, the fixed portion of securing apparatus 30 is detachably secured to the platform 10 to facilitate positioning of securing apparatus 30 around a body part. In some embodiments, each strap 30 includes an added component of flexibility such as a pliant band of material, a hook-and-loop fastener, or an elastic ring 44 that is incorporated along a length of the strap 30, interjacent the fixed and moveable portions. The adjustability component 44 allows for expansion and contraction of the securing apparatus 30, as they are being fitted, wrapped around, or removed from limbs and other body parts. The adjustability component 44 also accommodates expansion of a body part due to swelling, etc.

As described above, the straps 30 are easily applied to and removed from a body part of a subject. As may be recognized, the fixed portion of securing apparatus 30 may be secured to the inner 12 or outer 14 surfaces of the platform 10 by means of various bonding implements known in the art. These include, for example, glue, double sided tape, sonic (fusion) welding, radio frequency welding and the like. With the securing apparatus 30 in place about a subject's body part, the fastener 26 can be attached to a surface of a selected medical appliance. It will be understood, however, that the fastener 26 (including ends thereof) is localized to the upper plane 20 of the intervening protective platform 10. Fastener 26 is not employed in conjunction with the non-stick surface of the platform underside 16, which directly overlays the skin, fur or body tissue of a subject. As such, the stabilization device 8 of the present teachings avoids damage to or disintegration of the integument or tissue of a subject at the device 8 placement site.

The securing apparatus 30 can be fabricated of any sturdy yet flexible material that is not prone to breakage when pressure is applied. Such material can include, for example, woven nylon thread, cloth, or a Velcro® type material of a length that is sufficient to be fitted about a first body part, such as the arms, legs, waist, chest, or other body part of a human or an animal subject. Likewise, the securing apparatus 30 can comprise any appropriate width. In general, wider straps 30 are generally less likely to impinge on a wearer's skin or fur. Nonetheless, the securing apparatus 30 can be suitably sized and scaled to accommodate persons or animals of varying height and girth.

In various embodiments, the stabilization device 8 includes arms 22, 24 that protrude from an anterior section of the platform 10. The arms 22, 24 extend from the anterior section of the platform 10, along its edge, and terminate about a medial section of the platform or proximal to a closure segment 32 and strap 30. The substantially parallel arms 22, 24 can be formed in such a way as to define an aperture 36 interjacent to the arms 22, 24. The aperture 36 permits ease of access to operators for viewing and accurate insertion, for example, of intravenous catheter tubing and other medical appliances into a desired body site. The arms 22, 24 can optionally be marked with a medical device insertion line.

Figure 2:
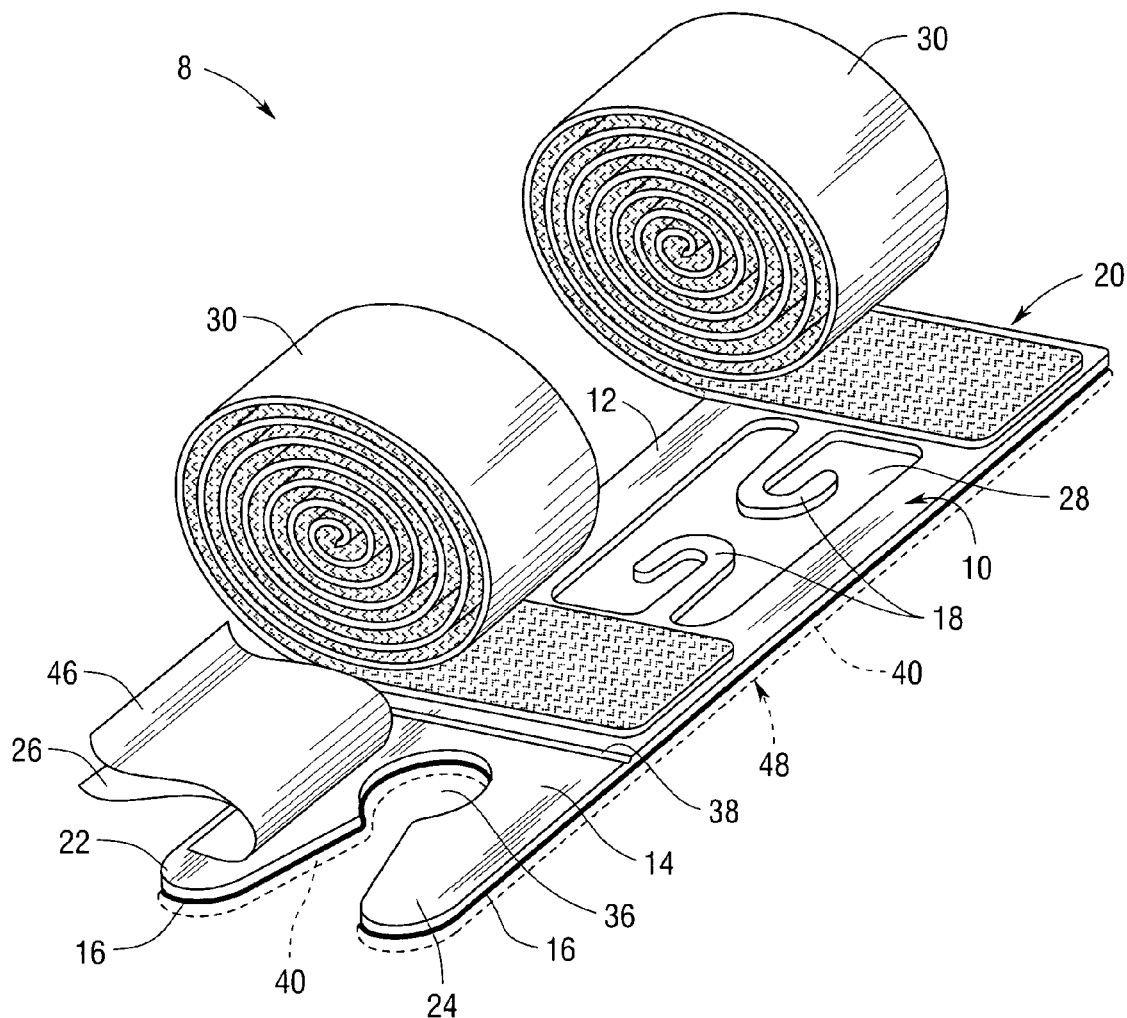
FIG. 2 is a perspective view of the stabilization device in accordance with the present teachings.
Figure 3:
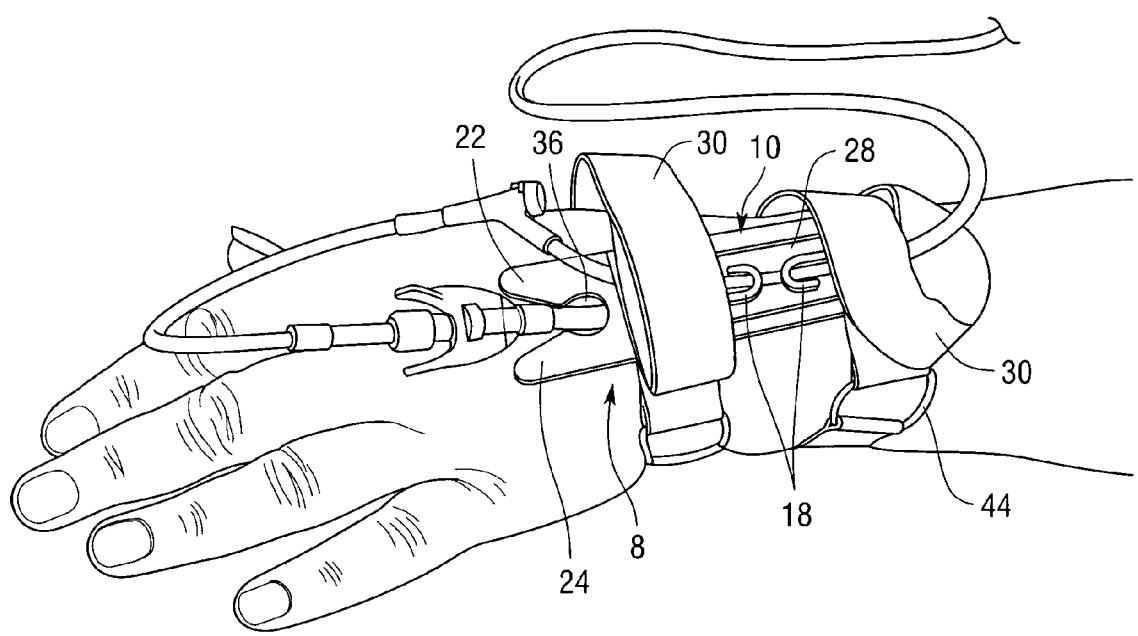
FIG. 3 is a perspective view depicting the stabilization device of the present teachings in use on a body part of a subject.
Figure 4A:
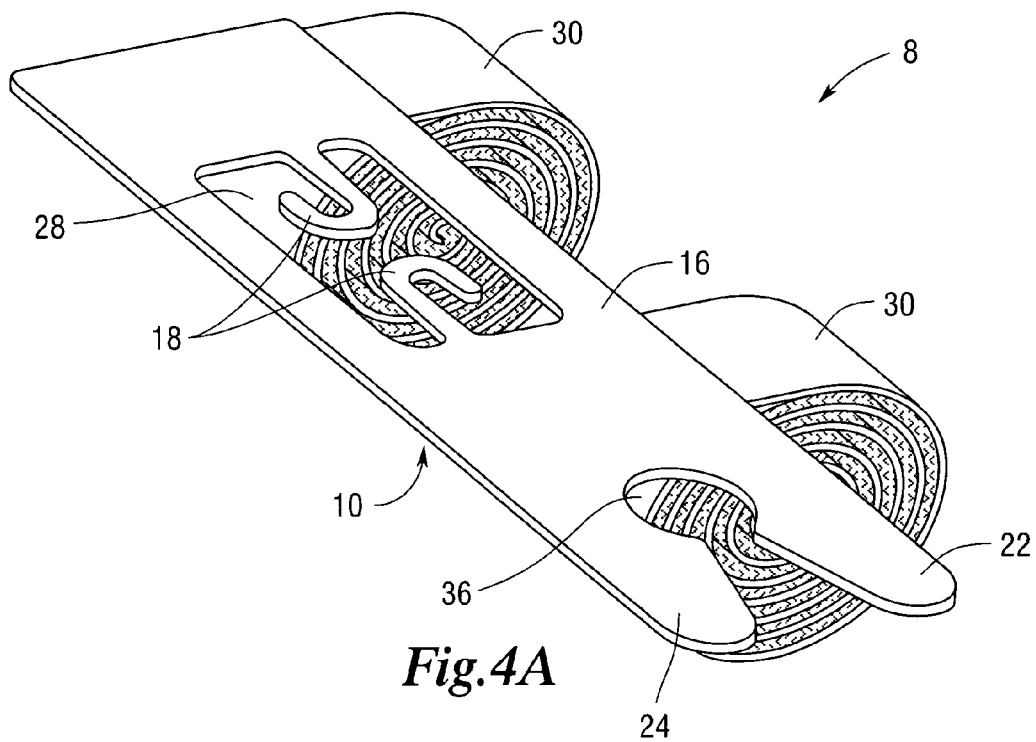
FIG. 4 is a perspective view depicting bottom surfaces of the stabilization device in accordance with the present teachings.
Figure 4B:
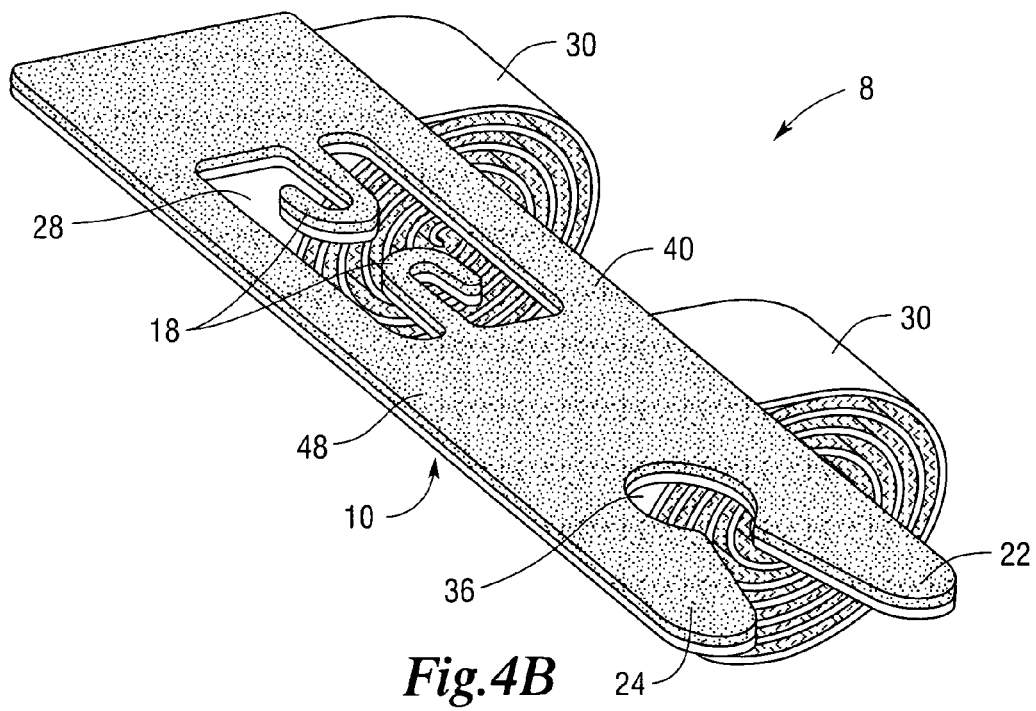

In various embodiments, the platform 10 defines one or more portals or windows 28 integrally incorporated within the inner surface 12 of the platform 10. In some embodiments, integrally formed hook members 18 protrude generally horizontally from within the portal 28 in platform 10, and define channels therein. Hook members 18 projecting from parallel surfaces within the window 28 of platform 10 are shown in FIGS. 2-4. The window 28 and hook members 18 permit convenient access to operators for viewing a medical appliance insertion or placement site and securing a medical appliance to the platform 10.

Hook members 18 positioned within the inner surface 12 of the platform 10 are normally used in applications such as intravenous tube line management. It will be appreciated that any number of portal 28 and hook member 18 configurations and orientations can be utilized as is necessary for a particular application. It is preferable that the platform 10 and hooks 18 (where employed) be integrally formed, for example, from a single mold or stamping technique. In some embodiments, one or more optional grooves or flexible portions 38 are disposed within the interior surface 12 of the platform 10. The grooves 38 permit the platform 10 to be flexed (as a result of motion, routine movements or care giving, etc.) while being worn. Such flexibility increases the comfort level of a subject.

Figure 5:
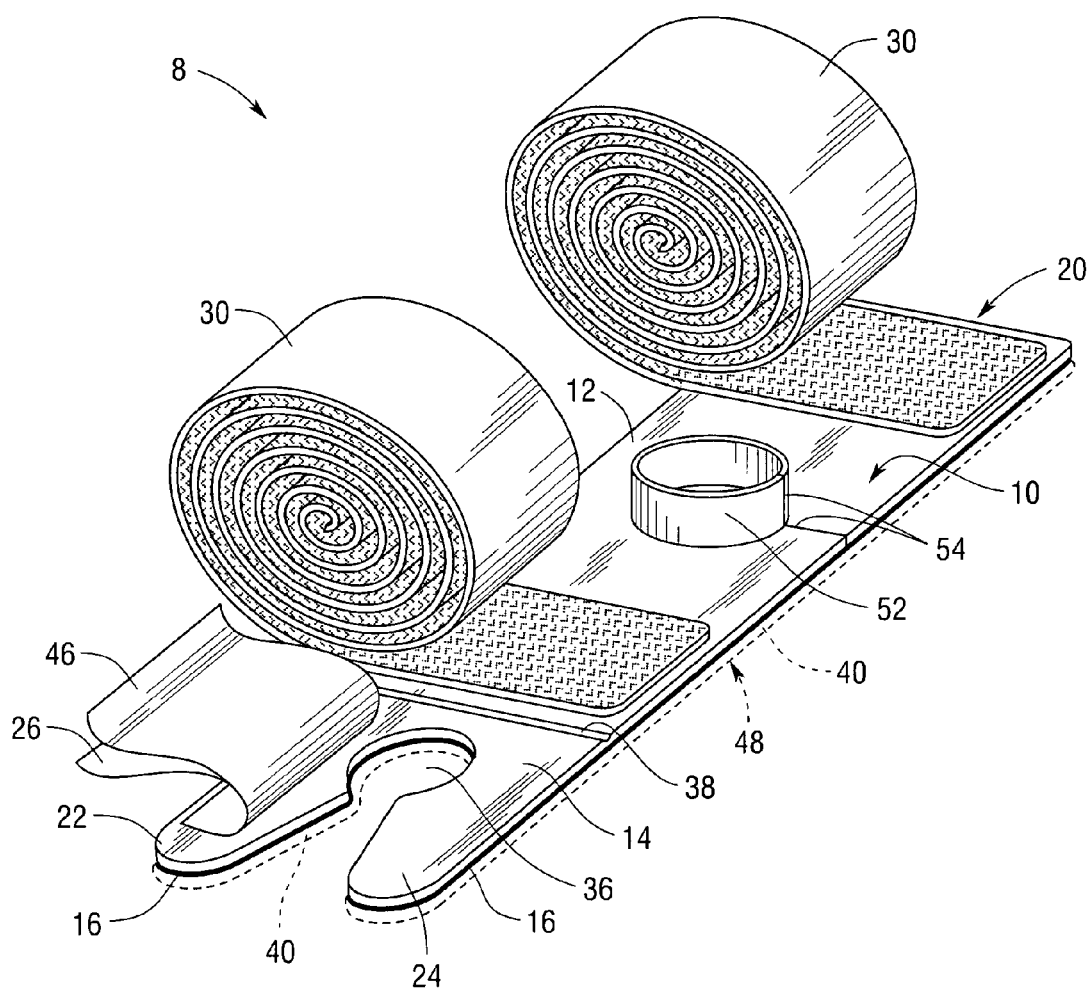
FIG. 5 is a perspective view of the stabilization device shown with a duct in accordance with the present teachings.

In contrast to the foregoing, hook members 18 are not typically employed in applications involving the umbilical stabilization of neonates or infants. In such applications, a stabilization device 8 incorporating an open duct 52 is utilized to support and stabilize the umbilicus. In various embodiments, the duct 52 is formed through an inner surface 12 of the platform 10 and projects upwardly therefrom. A second body part, such as an umbilical cord, is inserted through and is bounded by an interior circumference of the duct 52, permitting attachment of a medical appliance to the cord. As shown in FIG. 5, the stabilization device 8 can include a tubular duct 52 having an optional retractile seam 54 that traverses a surface of the duct. Extending from an upper portion of the duct 52, the seam 54 is formed through and also traverses an inner surface 12 of the platform 10, and terminates in an outer surface 14 or edge thereof. The retractile seam 54 is separable so as to enable placement of the stabilization device 8 about an umbilical cord without undue friction or chafing.

When the stabilization device 8 is in the "un-deployed" position, the closure members 34 of straps 30 are fastened or rolled up as seen, for example, in FIG. 2. In use, when deploying the device 8, an operator (e.g., healthcare personnel, patient, client, researcher, volunteer, or other individual) places the non-stick underside 16 of platform 10 against the skin or fur of a subject, sets a medical appliance to be utilized in place, and unfastens, unfurls or releases the straps, buckles, or hook and loop fasteners 30. The straps or other adjustable securing apparatus 30 of the stabilization device 8 are then arranged around the medical appliance and an appendage or other body part of the subject. Once deployed and secured in this fashion, the stabilization device 8 maintains any number of invasive and non-invasive medical appliances in place at a desired position.

In embodiments of the present teachings that utilize Velcro® type straps 30 fastened to the platform 10 (e.g., FIG. 3), for example, an operator releases and unfurls the closure member 34 of each strap 30, which is opposite the plane of a Velcro® swathed attachment area or closure segment 32 on the platform 10. The straps 30 are placed around the subject's appendage and a medical appliance, and are then attached to (e.g., by pressing against) the closure segment 32.

In some embodiments of the present teachings, a padding material 40 is detachably installed onto the bottom surface or underside 16 of platform 10. The padding material 40 comprises a non-adhesive surface for positioning adjacent a body part. If desired, the non-adhesive surface of padding 40 can incorporate various medicaments or emollients 48 intended for application to a subject's skin or fur. In some embodiments, a soft fabric (preferably non-woven) or hypoallergenic padding material 40, such as moleskin, is installed onto the underside 16 of platform 23. The supple padding material 40 provides an added layer of protection to irritated, hypersensitive, burnt, or broken skin when the stabilization device 8 is applied thereto.

Referring to FIG. 1, there is shown an optional retractable tray 42 secured to the upper plane 20 of the platform 10. The tray 42 is configured so as to allow a subject data tag 50 to be incorporated thereon. The tray 42 enables medical personnel to accurately identify a treatment to be administered to a patient, client, volunteer, or animal subject by means of the stabilization device 8. Moreover, the extendable tray 42 enables medical personnel to promptly retrieve or update health care information concerning a subject. If desired, a subject's personal, health, or medical treatment information can be conspicuously displayed within the tray 42. Alternatively, the information can be encoded on a data tag 50 to be readable by an electronic device (e.g., optical recognition scanner, bar code scanner or radio frequency identification scanner) to facilitate monitoring of the subject's compliance with a therapeutic regime without divulging individually identifiable health information.

In some embodiments, the device 8 is used to secure and stabilize an intravenous catheter and ported tubing, for example, which are subcutaneously inserted into the body of a subject. In this arrangement, the intravenous catheter is usually connected to an intravenous line. In use, an operator places the non-stick underside 16 of platform 10 against the skin or fur of a subject, positions and inserts the catheter into aperture 36 of platform 10, and introduces the catheter into the subject's circulatory system. Once the catheter is positioned by means of platform 10, the moveable section of fastener 26 can optionally be secured to a surface of the catheter and, if desired, to a parallel surface on the upper plane 20 of platform 10. With the intravenous catheter in place, the operator releases and enfolds the moveable portion of securing apparatus 30 and closure member 34 around a body part (e.g., a limb, arm, hand, wrist, or forearm) of the human or animal subject. After being released and placed in contact with subject's body part, the moveable portion of securing apparatus 30 is secured to the closure segment 32 on the platform 10.

In some embodiments, an operator threads a portion of the intravenous tubing through hook members 18 (that are suitably shaped to engage the catheter). In some embodiments, a "y" junction of the intravenous ported tubing or other medical appliance is secured between the moveable portion of one or more straps 30 and the platform 10 of stabilization device 8. As a result, the medical appliance remains in rigid contact with the platform 10 of stabilization device 8. Torque sufficient to lift a subject's limb can be applied to the stabilization device 8 without dislodgement of the catheter from the platform 10 or the subject's vein. Likewise, limited movements by the subject ordinarily do not result in removal of the catheter from its intravenous position or from the stabilization device 8. As such, the device 8 substantially decreases the risk of injury to a catheter site by securing and stabilizing the tubing associated with the site.

It will be appreciated that the preceding description is also applicable to systems and methods of using the present teachings in connection with other known invasive medical appliances such as catheter leads, pacemaker leads, defibrillator leads, and wound drainage systems. Likewise, the preceding description is generally applicable where the stabilization device 8 is deployed in connection with non-invasive medical appliances such as oxygen and cardiac monitoring systems. In non-invasive medical applications, however, it is unnecessary to pierce the integument or to enter the circulatory system.

It will be understood that certain invasive medical appliances known in the art such as urethral catheters and wound drainage systems currently lack a mechanism for securing the bags used to collect waste. As waste accumulates, these bags become anchors that exert unwanted pressure on the affected sites. Urethral damage and wound drainage complications frequently occur because these medical appliances are not secured. The stabilization device 8 of the present teachings can be used in conjunction with invasive medical appliances, such as those described above. Once deployed, the stabilization device 8 remains firmly connected to a medical appliance, preventing dislodgement of the appliance from its in vivo insertion site and related damage to the integument and underlying tissue.

The medical appliance stabilization device 8 according to the present teachings can be readily deployed in sterile, field and emergency situations. The device 8 provides a high level of stability, is inexpensive to produce, easy to use, durable, and easy to store.

The section headings used herein are for organizational purposes only and are not to be construed as limiting the subject matter described in any way.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

What is claimed is:

1. A non-adhesive based device for stabilizing a body part of a subject for medical appliance placement, the device comprising:

a generally planar platform having a perforate inner surface bordered by an outer surface, said inner and outer surfaces being disposed on an upper plane of said platform, the platform having an underside comprising a non-stick surface, said platform being suitably sized for positioning said non-stick surface adjacent a first body part while securing a medical appliance in engagement with the first body part, said platform including one or more securing apparatus attached to the platform for being arranged about the first body part for retaining the platform non-stick surface adjacent the first body part, said platform being interposed medial to the first body part and portions of said securing apparatus one or more arms extending from an anterior section of said platform, along an edge thereof, and terminating about a medial section of the platform;

a pad detachably installed on the underside of the platform, said pad having a non-stick surface for positioning adjacent said first body part; and a duct formed through the inner surface of said platform and projecting upwardly therefrom for positioning about a second body part, said duct comprising a perforate interior circumference without occlusive restraining elements, said duct stabilizing said second body part positioned therein while securing a medical appliance in engagement with the second body part, the duct supporting said second body part without injury thereto.

2. The device of claim 1 further comprising a fastener secured to the upper plane of the platform for retaining the medical appliance in engagement with said platform.

3. The device of claim 1 wherein said detachable pad further includes a medicament or an emollient disposed on the non-stick surface thereof.

4. The device of claim 1 further comprising a retractable tray secured to the upper plane of the platform, said tray incorporating subject identification and health data.

5. The device of claim 1 wherein said platform is translucent to permit observation therethrough.

6. The device of claim 5 wherein said platform is fabricated from a resin, plastic, polycarbonate, polymer, rubber, foam, acrylic, nylon, polystyrene, or composite material.

7. The device of claim 1 wherein said securing apparatus includes a flexible ring incorporated along a length thereof for accommodating an expansion or contraction of said securing apparatus.

8. The device of claim 1 wherein said duct further comprises a seam formed through a surface of said duct and through the inner surface of said platform, the seam extending outwardly from said platform inner surface.

9. A method for stabilizing a body part of a subject for medical appliance placement, the method comprising:
    employing a non-adhesive based device comprising a generally planar platform having a perforate inner surface bordered by an outer surface, said inner and outer surfaces being disposed on an upper plane of said platform, one or more arms extending from an anterior section of said platform, along an edge thereof, and terminating about a medial section of the platform, said platform having an underside comprising a non-stick surface, said platform being suitably sized for positioning said non-stick surface adjacent a first body part of a subject, and having one or more retractable securing apparatus attached to the platform for being arranged about the first body part for retaining the non-stick surface adjacent the first body part, said platform being interposed medial to the first body part and portions of said securing apparatus, a duct being formed through the inner surface of the platform and projecting upwardly therefrom for positioning about a second body part, said duct comprising a perforate interior circumference without occlusive restraining elements, said duct stabilizing said second body part positioned therein while securing a medical appliance in engagement with the second body part, the duct supporting said second body part without injury thereto;
    placing said non-stick surface of the device platform at a desired site adjacent the first body part;
    positioning a medical appliance for engagement with said device;
    contacting the second body part with the medical appliance;
    releasing and placing said retractable securing apparatus about the first body part; and
    fastening said retractable securing apparatus to said device platform for retaining the first body part in contact with said medical appliance.

10. The method of claim 9 wherein said contacting step further comprises positioning said medical appliance onto integument of said second body part.

11. The method of claim 9 wherein said contacting step further comprises subcutaneously introducing said medical appliance into said second body part.

12. The method of claim 9 further comprising the step of employing a fastener secured to the upper plane of the platform for retaining the medical appliance in engagement with said platform.

13. The method of claim 9 further comprising the step of employing a pad being detachably installed onto the underside of the platform, said pad having a non-stick surface for positioning adjacent said first body part.

14. The method of claim 9 further comprising the step of employing a pad being detachably installed onto the underside of the platform, said pad having a non-stick surface for positioning adjacent said first body part, said non-stick surface including a medicament or an emollient disposed thereon.

15. The method of claim 9 further comprising the step of employing a retractable tray secured to the upper plane of the platform, said tray incorporating subject identification and health data.

16. The method of claim 9 further comprising the step of employing a flexible ring incorporated along a length of said securing apparatus for accommodating an expansion or contraction of said securing apparatus.

* * * * *